United States Patent [19]

Takemoto et al.

[11] Patent Number: 5,663,382
[45] Date of Patent: Sep. 2, 1997

[54] PROCESS FOR PREPARING 3-METHYLTETRAHYDROFURAN

[75] Inventors: Masaki Takemoto; Yoshikazu Shima; Takafumi Abe, all of Niigata, Japan

[73] Assignee: Mitsubishi Gas Chemical Company, Inc., Tokyo, Japan

[21] Appl. No.: 729,384

[22] Filed: Oct. 11, 1996

[30] Foreign Application Priority Data

Nov. 7, 1995 [JP] Japan .................................. 7-288245

[51] Int. Cl.$^6$ .................................................. C07D 307/08
[52] U.S. Cl. .................................................. 549/508
[58] Field of Search ................................................ 549/508

[56] References Cited

U.S. PATENT DOCUMENTS 3,859,369  1/1975  Copelin ................................ 549/508

Primary Examiner—Johann Richter
Assistant Examiner—Laura L. Stockton
Attorney, Agent, or Firm—Frishauf, Holtz, Goodman, Langer & Chick, P.C.

[57] ABSTRACT

A process for preparing 3-methyltetrahydrofuran is herein disclosed which comprises reacting a methacrylic acid ester with carbon monoxide and a lower aliphatic alcohol to obtain a methylsuccinic acid diester, and hydrogenating and dehydrating/cyclizing this methylsuccinic acid diester. According to this process, 3-methyltetrahydrofuran can efficiently be obtained from inexpensive starting materials.

5 Claims, No Drawings

PROCESS FOR PREPARING 3-METHYLTETRAHYDROFURAN

BACKGROUND OF THE INVENTION

1. Field of the Invention

The present invention relates to a novel process for preparing 3-methyltetrahydrofuran, which is a useful substance as a comonomer of polytetramethylene ether glycol which is a raw material of elastic fibers called spandex fibers, or as a solvent for a specific use purpose.

2. Description of the Related Arts

As preparation methods of 3-methyltetrahydrofuran, various methods have heretofore been disclosed, and for example, there are a method which comprises the hydrogenation of citric acid (EP Disclosure No. 277562) and another method which comprises the hydrogenation of 4-hydroxy-2-methylbutane-1,2-epoxide (U.S. Pat. No. 3,956,318). However, these starting materials are less easily available, and therefore these methods are industrially impractical. In addition, a method which comprises the hydrogenation of methylmaleic acid or methylsuccinic acid (Japanese Patent Publication No. 9463/1974) has also been disclosed, but this starting material is scarcely available and what is worse, conditions for the hydrogenation are also severe. These inconveniences make its industrial practice difficult.

Furthermore, there is a method which comprises partially hydrogenating 1,4-butynediol to form 2-buten-,1,4-diol, hydroformylating and hydrogenating the thus formed 2-buten- 1,4-diol to obtain 2-methyl-1,4-butanediol (U.S. Pat. No. 3,859,369), and then dehydrating/cyclizing this product in the presence of an acid catalyst to obtain 3-methyltetrahydrofuran. However, this method has some drawbacks. For example, the selectivity of 2-buten-1,4-diol by the partial hydrogenation of 1,4-butynediol is not sufficiently high, and the yield of the desired hydroformylation product of an internal olefin such as 2-buten-,1,4-diol is not sufficiently high, either.

In addition, a method has been disclosed which comprises the hydrogenation of β-formyl isobutyrate to obtain 3-methyltetrahydrofuran or 2-methyl-1,4-butanediol (Japanese Patent Application Laid-open No. 219981/1994). β-formyl isobutyrate which is a starting material in this method can be synthesized in a known manner such as the hydroformylation of a methacrylic acid ester [Bull. Chem. Soc. Japan, Vol. 50, p. 2351 (1977)], but the production of an α-isomer whose boiling point is close to that of β-formyl isobutyrate is not avoidable. Thus, a large amount of energy is required for its separation, and for this reason, the disclosed method is not considered to be industrially advantageous.

Under such circumstances, the present invention has been developed to solve the problems in the above-mentioned various manufacturing methods of 3-methyltetrahydrofuran, and an object of the present invention is to provide a process for preparing 3-methyltetrahydrofuran by an industrially advantageous procedure.

SUMMARY OF THE INVENTION

The present inventors have intensively researched with the intention of solving the above-mentioned problems. As a result, it has been found that the object of the present invention can be achieved by first synthesizing methylsuccinic acid diester from a methacrylic acid ester, carbon monoxide and a lower aliphatic alcohol as materials, and then hydrogenating and simultaneously dehydrating/cyclizing this diester to obtain 3-methyltetrahydrofuran. The present invention has been completed on the basis of this found knowledge.

That is to say, the present invention provides a process for preparing 3-methyltetrahydrofuran which comprises a step 1 of reacting a methacrylic acid ester with carbon monoxide and a lower aliphatic alcohol to synthesize a methylsuccinic acid diester, and a step 2 of hydrogenating and dehydrating/cyclizing the methylsuccinic acid diester which is the product of the step 1.

DESCRIPTION OF THE PREFERRED EMBODIMENTS

Next, a process of the present invention will be described in detail.

A methacrylic acid ester which is a starting material in the present invention can be manufactured industrially in large quantities as a monomer of polymethacrylates, and so it is inexpensively available. Carbon monoxide which is another material can be mass-produced as a water gas or an iron manufacturing gas, and so, needless to say, it is easily available. Furthermore, a lower aliphatic alcohol can be recovered after the hydrogenation reaction of a methylsuccinic acid diester in a step 2, and in principle, it is not consumed. As understood from the above, according to the process of the present invention, the materials which are all inexpensively available can be used, and so 3-methyltetrahydrofuran can be prepared in a high selectivity. In consequence, the process of the present invention has an industrially extremely high significance. The preparation process of 3-methyltetrahydrofuran according to the present invention can schematically be shown by the following reaction formulae

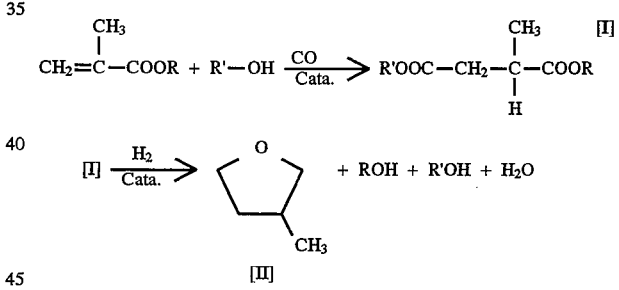

wherein R and R' are each an alkyl group; [I] is a methylsuccinic acid diester; and [II] is 3-methyltetrahydrofuran. Here, R is preferably an alkyl group having 1 to 8 carbon atoms, and R' is preferably an alkyl group having 1 to 8 carbon atoms.

The reaction of the methacrylic acid ester with carbon monoxide and the lower aliphatic alcohol in the step 1 of the present invention can be carried out under various conditions, but preferably, the reaction is done in the presence of an element belonging to any of the group 8 to 10 of the periodic table, i.e., a catalyst containing an element belonging to any of the group 8 to 10 of the periodic table, or its compound. The methacrylic acid ester which can be used in this reaction is usually an alkyl methacrylate (wherein an alkyl group has 1 to 8 carbon atoms), and typical examples of the alkyl methacrylate include methyl methacrylate, ethyl methacrylate, propyl methacrylate, isopropyl methacrylate and butyl methacrylate. They are all usable from the viewpoint of reactivity, but in view of easy availability, methyl methacrylate is suitable. Furthermore, the lower aliphatic alcohol is usually an aliphatic alcohol having 1 to 8 carbon atoms, and typical examples of the lower aliphatic alcohol include methanol, ethanol, n-propanol, iso-propanol and n-butanol.

A practical system in the step 1 of the present invention may suitably be selected in compliance with various situations, but a homogeneous liquid phase system is preferable. In this homogeneous liquid phase system, the methacrylic acid ester as the material is mixed with the lower aliphatic alcohol and the catalytic component, and the mixture is then treated at a predetermined temperature for a predetermined period of time under an increased pressure of carbon monoxide to accomplish the above-mentioned step 1. No particular restriction is put on a molar ratio of the lower aliphatic alcohol to the methacrylic acid ester, but this ratio is preferably in the range of 0.1 to 50 mol, more preferably 0.5 to 10 mol. In addition, carbon monoxide is consumed as the reaction material, and it simultaneously plays the role of highly maintaining the activity of an element belonging to any of the group 8 to 10 of the periodic table or its compound which can be used as the catalyst. In this step 1, therefore, the reaction is carried out under an increased pressure of usually 1 to 300 kg/cm$^2$ (gauge pressure), preferably 5 to 200 kg/cm$^2$ (gauge pressure). Carbon monoxide which can be used in the process of the present invention is never required to be highly pure, and so carbon monoxide containing methane, hydrogen, nitrogen or the like can also be used without any problem, so long as the partial pressure of carbon monoxide can be secured. Examples of the element belonging to any of the groups 8 to 10 of the periodic table which can be used as the catalyst include iron, cobalt, nickel, ruthenium, rhodium, palladium, osmium, iridium and platinum, and they can be used as the catalyst singly or in the form of a mixture of two or more thereof. Of these compounds enumerated above, cobalt and ruthenium are particularly suitable as the catalytic component. The compound containing the element in the groups 8 to 10 of the periodic table which can be used as the catalyst can be used in the form of a halide, a salt of an organic acid or an inorganic acid, a carbonyl compound or a phosphine coordination compound, but the carbonyl compound is particularly suitable. The amount of the element in the groups 8 to 10 of the periodic table which can be used as the catalyst in the present invention is usually in the range of 0.1 to 200 mmol, preferably 1 to 50 mmol with respect to 1000 ml of the reaction solution.

Furthermore, in order to increase a reaction rate, a suitable promotor can be added to the system. Examples of a compound which can be used as the promotor include tertiary amines, tertiary phosphine compounds, and organic and inorganic halides, and they may be used singly or in a combination of two or more thereof.

Typical examples of the tertiary amines include trimethylamine, triethylamine, N,N,N',N'-tetramethylethylenediamine, pyridine, N,N-dimethylaminopyridine and lutidine.

Typical examples of the tertiary phosphine compounds include triphenylphosphine, tributylphosphine, tricyclohexylphosphine, bis(diphenylphosphino)ethane, bis(diphenylphosphino)propane and bis(diphenylphosphino)butane.

Typical examples of the organic halides include tetramethylammonium iodide, tetramethylammonium bromide, tetramethylammonium chloride, methyltriphenylphosphonium iodide, methyltriphenylphosphonium bromide, methyltriphenylphosphonium chloride, methyl iodide, methyl bromide, ethyl iodide and ethyl bromide.

Typical examples of the inorganic halides include lithium iodide, lithium bromide, lithium chloride, sodium iodide, sodium bromide, sodium chloride, potassium iodide, potassium bromide, potassium chloride, magnesium iodide, magnesium bromide and magnesium chloride.

The combination and the amount of these promotors can be decided in compliance with the selected catalyst.

In the practice of the process of the present invention, it is possible to use a reaction solvent. As the reaction solvent, the reaction material itself can utilized as the reaction solvent, but no particular restriction is put on a kind of the reaction solvent, so long as it is stable in the reaction system and does not disturb the desired reaction. Thus, the reaction solvent can be selected from the group consisting of aliphatic hydrocarbons, aromatic hydrocarbons, ethers, ketones, esters and amides. A reaction temperature in the process of the present invention is usually in the range of 50° to 350° C., preferably 100° to 250° C.

The methylsuccinic acid diester which is a reaction product in the step 1 of the present invention is separated from the catalytic component by an operation such as distillation or extraction if necessary, and it is then fed to the following hydrogenation and dehydration/cyclization reaction (the step 2).

The hydrogenation and the dehydration/cyclization reaction in the step 2 of the present invention can be allowed to proceed under various conditions, but it is preferable that they proceed in the presence of a catalyst. The suitable catalyst contains at least one selected from the group consisting of copper, copper compounds, metals in the groups 7 to 10 of the periodic table, and metallic compounds thereof. More specifically, examples of the principal effective component of the catalyst for the reaction in the step 2 include copper, cobalt, nickel, iron, rhenium, palladium, ruthenium, platinum and rhodium. Furthermore, a promotor can effectively be used, and the suitable promotor is a solid acidic component containing chromium, molybdenum, manganese, barium, magnesium, silicon or aluminum. The catalyst which is particularly suitable for the reaction in the step 2 is a catalyst usually called copper-chromite containing copper as the principal component and containing manganese or barium as the promotor component. The hydrogenation and the dehydration/cyclization reaction in the step 2 of the present invention can be carried out at a reaction temperature of about 100° to 300° C. under a reaction pressure of about 20 to 200 kg/cm$^2$ (gauge pressure), depending upon the selected catalytic component and the reaction conditions. In the case that the particularly suitable copper-chromite is used as the catalyst in the step 2 of the present invention, the reaction temperature is suitably in the range of 180° to 280° C., and the reaction pressure is suitably in the range of 50 to 200 kg/cm$^2$ (gauge pressure). Hydrogen which can be used in the reaction is preferably pure hydrogen, but hydrogen containing methane, nitrogen or the like is also usable.

As the catalyst for use in the hydrogenation reaction in the step 2, a copper-chromium-manganese (or barium) catalyst is preferable, and for example, it can be prepared by the following procedure.

(1) Solid cupric oxide (CuO), chromium oxide ($Cr_2O_3$) and manganese dioxide ($MnO_2$) [or barium oxide (BaO)] are mixed with one another, and graphite or the like is further added as a lubricant. After sufficient mixing, the mixture is molded in a usual manner, and the molded article is calcined at a high temperature, crushed to a suitable size, and then used.

(2) Aqueous ammonia is added to an aqueous solution containing dissolved ammonium bichromate, and another aqueous solution in which cupric nitrate (or cupric sulfate)

and manganese nitrate (or manganese sulfate) or barium nitrate are dissolved is then added dropwise to the above-mentioned aqueous solution with stirring. The resulting precipitate is washed with water, dried, and then calcined at a temperature of about 350° C. in air. The thus calcined powder obtained in this manner can directly be used for the reaction, but a suitable binder and lubricant can be added to this calcined powder, and they can sufficiently be mixed, molded, and then used.

A weight ratio of the respective components contained in the copper-chromium-manganese (or barium) catalyst obtained in the manner of the above-mentioned (1) or (2), i.e., $CuO:Cr_2O_3:MnO_2$ (or BaO) is preferably in the range of 20–85:15–75:1–15. The catalyst may be used in the form of powder or tablets, and the optimum form of the catalyst can be selected in compliance with its use purpose. Prior to use in the reaction, the catalyst can be subjected to a suitable activation treatment such a treatment in a hydrogen atmosphere at about 200° C. In the practice of the reaction in the step 2 of the present invention, the amount of hydrogen is 4 mol or more, preferably 6 to 60 mol per mol of the ester supplied for reaction.

In the present invention, the reaction solution containing 3-methyltetrahydrofuran prepared by the hydrogenation and the dehydration/cyclization reaction is subjected to a usual distillation operation to separate and purify 3-methyltetrahydrofuran, whereby desired 3-methyltetrahydrofuran can easily be obtained.

According to the present invention, the treatments in the respective steps proceed in high yields, and what is better, 3-methyltetrahydrofuran can efficiently be obtained from the inexpensive starting materials. Accordingly, the present invention has an industrially extremely high merit.

Next, the present invention will be described in more detail with reference to examples, but the scope of the present invention should not be limited to these examples.
(Step 1)

EXAMPLE 1

In a 100-ml stainless steel autoclave equipped with a thermometer and a pressure gauge were placed $3.0 \times 10^{-2}$ mol of methyl methacrylate, 0.2 mol of methanol, $1.0 \times 10^{-4}$ mol of $Ru_3(CO)_{12}$ as a catalyst and $5.0 \times 10^{-4}$ mol of methyltriphenylphosphonium iodide ($Ph_3PMeI$) as a promotor. The reactor was sufficiently purged with a carbon monoxide gas, and the carbon monoxide gas was filled into the reactor up to 20 kg/cm$^2$ (gauge pressure). Next, the reactor was immersed in an oil bath maintained at 165° C., and a reaction solution was then stirred by a magnetic stirrer, whereby reaction was carried out for 4 hours. The reaction solution was analyzed by gas chromatography, and as a result, it was apparent that the conversion of methyl methacrylate was 54%, and the selectivity of dimethyl methylsuccinate was 88.0% and the selectivity of methyl isobutyrate was 4.0%.

EXAMPLE 2

The same procedure as in Example 1 was repeated except that $1.5 \times 10^{-3}$ mol of $Co_2(CO)_8$ as a catalyst and $3.0 \times 10^{-3}$ mol of pyridine as a promotor were used and carbon monoxide was filled up to a pressure of 50 kg/cm$^2$ (gauge pressure). As the results of analysis, the conversion of methyl methacrylate was 40%, and the selectivity of dimethyl ethyl methylsuccinate was 80.5% and the selectivity of methyl isobutyrate was 3.2%.
(Step 2)

EXAMPLE 3

A stainless steel reaction tube having an inner diameter of 15 mm and a length of 300 mm was used as a hydrogenation reactor, and 10 g of a copper-chromite catalyst (G-99C, made by Nissan Gardler Co., Ltd.) having a uniform size of 10 to 20 mesh was filled into the reaction tube. Next, the catalyst was reduced at 150° to 200° C. with a nitrogen-hydrogen mixing gas containing 0.5 to 5% by volume of hydrogen in a usual manner under such conditions as not to form hot spots.

The catalytic component was separated and the dimethyl methylsuccinate was isolated in a usual manner (distillation under reduced pressure) from the reaction solution obtained in Example 1. Next, 70 parts by weight of the xylenes (a mixture of xylene isomers and ethylbenzene) was added to 30 parts by weight of this dimethyl methylsuccinate to prepare a feed material for hydrogenation and dehydration/cyclization reaction. The feed gas to the hydrogenation reactor was switched to pure hydrogen, and in this case, pressure was 160 kg/cm$^2$ (gauge pressure), the space velocity (SV) of the purge gas was 500 hr$^{-1}$, and the temperature of the catalyst layer was 230° C. The reaction material was fed to the reaction tube through its upper portion at a feed rate of 3.3 g per hour. After cooling, the reaction product was subjected to gas-liquid separation, and the resulting liquid phase portion was then analyzed by gas chromatography. After 5 hours from the start of the reaction, the reaction product was collected for 1 hour, and then analyzed. As a result, the yield of 3-methyltetrahydrofuran was 95.2%, and that of 2-methylbutanediol was 0.4%.

What is claimed is:

1. A process for preparing 3-methyltetrahydrofuran which comprises a step 1 of reacting a methacrylic acid ester with carbon monoxide and a lower aliphatic alcohol to synthesize a methylsuccinic acid diester, and a step 2 of hydrogenating and dehydrating/cyclizing the methylsuccinic acid diester which is the product of the step 1.

2. The process for preparing 3-methyltetrahydrofuran according to claim 1 wherein the reaction of the methacrylic acid ester with carbon monoxide and the lower aliphatic alcohol is carried out in the presence of an element belonging to any of the group 8 to 10 of the periodic table.

3. The process for preparing 3-methyltetrahydrofuran according to claim 2 wherein the element belonging to any of the group 8 to 10 of the periodic table is cobalt or ruthenium.

4. The process for preparing 3-methyltetrahydrofuran according to claim 1 wherein the hydrogenation reaction in the step 2 is carried out in the presence of at least one selected from the group consisting of copper, copper compounds, metals in the groups 7 to 10 of the periodic table, and metallic compounds thereof.

5. The process for preparing 3-methyltetrahydrofuran according to claim 4 wherein the hydrogenation reaction in the step 2 is carried out in the presence of a hydrogenation catalyst comprising copper-chromite.

* * * * *